United States Patent
Polonka et al.

(10) Patent No.: US 8,119,698 B2
(45) Date of Patent: Feb. 21, 2012

(54) SUNSCREEN FORMULA VANISHING CREAM

(75) Inventors: Jack Polonka, Peekskill, NY (US);
Xiaoling Wei, Woodbridge, NJ (US);
John Brian Bartolone, Bridgeport, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 883 days.

(21) Appl. No.: 12/164,138

(22) Filed: Jun. 30, 2008

(65) Prior Publication Data
US 2009/0324655 A1 Dec. 31, 2009

(51) Int. Cl.
*A61K 47/30* (2006.01)
*A61K 31/44* (2006.01)
*A61K 47/00* (2006.01)

(52) U.S. Cl. ............... 514/772.3; 514/356; 514/784
(58) Field of Classification Search ............. 514/772.3, 514/356, 784
See application file for complete search history.

(56) References Cited

U.S. PATENT DOCUMENTS

| | | | |
|---|---|---|---|
| 4,731,242 A | 3/1988 | Palinczar | |
| 5,246,613 A * | 9/1993 | Gilbert et al. | 510/138 |
| 5,264,207 A | 11/1993 | Bommelaer et al. | |
| 5,733,531 A | 3/1998 | Mitchnick et al. | |
| 5,783,657 A | 7/1998 | Pavlin et al. | |
| 5,972,359 A | 10/1999 | Sine et al. | |
| 5,997,890 A | 12/1999 | Sine et al. | |
| 5,998,570 A | 12/1999 | Pavlin et al. | |
| 6,036,945 A | 3/2000 | Deblasi et al. | |
| 6,174,533 B1 | 1/2001 | SaNogueira, Jr. et al. | |
| 6,242,509 B1 | 6/2001 | Berger et al. | |
| 6,280,710 B1 | 8/2001 | Deblasi et al. | |
| 6,362,146 B1 * | 3/2002 | Macaulay | 510/159 |
| 6,399,713 B1 | 6/2002 | MacQueen et al. | |
| 6,402,408 B1 | 6/2002 | Ferrari | |
| 6,492,458 B1 | 12/2002 | Pavlin | |
| 6,552,160 B2 | 4/2003 | Pavlin | |
| 6,825,161 B2 * | 11/2004 | Shefer et al. | 510/438 |
| 6,835,399 B2 | 12/2004 | Collin | |
| 6,870,011 B2 | 3/2005 | MacQueen et al. | |
| 6,875,245 B2 | 4/2005 | Pavlin | |
| 7,253,249 B2 | 8/2007 | Pavlin | |
| 7,264,795 B2 | 9/2007 | Pflucker et al. | |
| 7,329,719 B2 | 2/2008 | Pavlin | |
| 7,351,418 B2 | 4/2008 | Collin | |
| 7,776,350 B2 * | 8/2010 | Polonka et al. | 424/401 |
| 7,892,524 B2 * | 2/2011 | Polonka et al. | 424/59 |
| 7,914,772 B2 * | 3/2011 | Polonka et al. | 424/59 |
| 2002/0155073 A1 | 10/2002 | Fankhauser et al. | |
| 2003/0113357 A1 * | 6/2003 | Bell et al. | 424/401 |
| 2005/0037087 A1 | 2/2005 | Lapidot et al. | |
| 2005/0163730 A1 | 7/2005 | Rosevear et al. | |
| 2005/0163813 A1 | 7/2005 | Kosbach et al. | |
| 2005/0249684 A1 | 11/2005 | Dobkowski et al. | |
| 2005/0276833 A1 | 12/2005 | Fowler | |
| 2006/0099168 A1 | 5/2006 | Corzani et al. | |
| 2006/0280763 A1 | 12/2006 | Yoshida et al. | |
| 2007/0093619 A1 * | 4/2007 | Bui et al. | 525/477 |
| 2007/0212315 A1 | 9/2007 | Pastor et al. | |
| 2008/0115846 A1 | 5/2008 | Josso et al. | |
| 2008/0274149 A1 * | 11/2008 | Seiler et al. | 424/401 |
| 2009/0016971 A1 | 1/2009 | Gaudry et al. | |
| 2009/0117060 A1 | 5/2009 | Golz-Berner et al. | |

FOREIGN PATENT DOCUMENTS

| | | |
|---|---|---|
| AU | 1999 44705 B2 | 10/1999 |
| GB | 2230186 A * | 10/1990 |
| WO | WO 9528912 A1 * | 11/1995 |
| WO | 99/63965 | 12/1999 |
| WO | 01/87847 A2 | 11/2001 |
| WO | 2006/083843 | 8/2006 |
| WO | WO 2007048464 A1 * | 5/2007 |
| WO | 2009/007264 A2 | 1/2009 |

OTHER PUBLICATIONS

Arizona Chemical, Sylavclear AF1900V-Material Safety Data Sheet, printed from http://www.arizonachemical.com/Global/MSDS/US_MSDS/SYLVACLEAR%20AF1900V_MSDS.pdf, Aug. 14, 2008, 5 pages.*
Arizona Chemical, Beautiful chemistry—Specialty Polymeric Gellants for Personal Care & Cosmetics, Oct. 16, 2006, printed from http://web.archive.org/web/20061016075226/http://www.arizonachemical.com/gellants/pdfs/personalcare_cosmetics_brochure.pdf, 5 pages.*
Co-Pending Application: Polonka et al.; Entitled: Sunscreen Composite Particles and Porous Particles in Cosmetic Compositions, U.S. Appl. No. 12/164,137.
International Search Report PCT/EP2009/057155.

* cited by examiner

*Primary Examiner* — Sreeni Padmanabhan
*Assistant Examiner* — Gigi Huang
(74) *Attorney, Agent, or Firm* — Milton L. Honig

(57) ABSTRACT

A cosmetic composition is provided which is a vanishing cream structured with 0.5 to 50% by weight of $C_{12}$-$C_{20}$ fatty acid, 0.1 to 20% by weight of $C_{12}$-$C_{20}$ fatty acid salt and hydrophilic composite particles with organic sunscreen agent. The hydrophilic composite particles are formed as a composite of sunscreen agent and a binder in a relative weight ratio of about 5:1 to about 1:10. The composition exhibits relatively high SPF photoprotection while maintaining excellent skinfeel aesthetics.

4 Claims, No Drawings

SUNSCREEN FORMULA VANISHING CREAM

BACKGROUND OF THE INVENTION

1. Field of the Invention

The invention concerns a form of vanishing cream as a cosmetic composition delivering a high level of photoprotection with good skin aesthetics.

2. The Related Art

Vanishing creams are quite popular around the world. They spread easily on the skin giving a thin, semi-matte film which seems to disappear or "vanish". They are also used to counteract shine which may arise from overactive sebaceous glands. Moreover, these creams counteract skin dryness to alleviate flaking, cracking and roughness.

The creams are formulated with high levels of stearic acid suspended in water by an emulsifying agent. Typically the emulsifying agent is a potassium or sodium soap formed by in situ reaction of caustic potash or other alkali on a portion of the stearic acid.

Ultraviolet radiation can be damaging to skin. Immediate damage may be in the form of erythema. More long term is the concern of initiating cancerous growth. For these reasons, photoprotective agents known as sunscreens have been incorporated into cosmetic products. When the cosmetic product is a vanishing cream, we have found it is much more difficult to incorporate any high level of photoprotection while still maintaining desirable skinfeel properties.

Accordingly, the present invention is focused upon cosmetic compositions, particularly vanishing creams, exhibiting not only a high level of photoprotection but also good aesthetic properties.

SUMMARY OF THE INVENTION

A cosmetic composition is provided which includes:
(i) from 5 to 50% by weight of a $C_{12}$-$C_{20}$ fatty acid;
(ii) from 0.1 to 20% by weight of a $C_{12}$-$C_{20}$ fatty acid salt; and
(iii) from about 0.1 to about 20% by weight of hydrophilic composite particles formed of an organic sunscreen agent and a binder in a relative weight ratio of about 5:1 to about 1:10.

DETAILED DESCRIPTION OF THE INVENTION

Now it has been found that cosmetic vanishing creams can be formulated to achieve a significant level of photoprotective performance without any loss of skinfeel aesthetics. Photoprotection is accomplished through hydrophilic composite particles formed of a binder and an organic sunscreen agent.

Fatty Acid Structurant

A first structurant component of vanishing cream compositions of the present invention is one or more of a $C_{12}$-$C_{20}$ fatty acid. Stearic acid is particularly preferred. Amounts of fatty acid will range from 5 to 50%, preferably from 7 to 40%, more preferably from 10 to 25%, optimally from 12 to 20% by weight of the composition.

Advantageously the stearic acid may be present as asymmetric solid particles. Asymmetric is understood to mean that at least two of three dimensions on a majority of the particles are not size identical. These particles can be oval or plate-like. Average particle size along greatest length may range from about 0.01 to about 500 micron and preferably from about 1 to about 100 micron. The particles are employed in the composition to impart a cream-like viscosity. By virtue of being asymmetric, the particles deliver high skin friction.

A second component of the fatty acid structurant will be a salt of a $C_{12}$-$C_{20}$ fatty acid in amounts ranging from about 0.1 to about 20%, preferably from about 0.5 to about 10%, optimally from about 1 to about 4% by weight of the composition. Typically the salt forming cation may be selected from sodium, potassium, ammonium and triethanolammonium cations. Most preferred are potassium salts, particularly potassium stearate.

Hydrophilic Composite Particles of Sunscreen Agent

Composite particles of the present invention will have a hydrophilic outer surface. Hydrophilicity may be achieved through use of a hydrophilic binder or via a hydrophilic coating such as a silica or alumina coating. The binder may be hydrophilic or hydrophobic. Suitable categories of binder are polymers such as polyacrylates, polyvinylpyrrolidones, polyesters, polyamides, polyethers, polyolefins, polysaccharides including cellulose derivatives, starches, clays, hydrocarbons and combinations thereof. Sunscreen agents can either be dispersed throughout the binder or can be formed as a core surrounded by binder.

Relative weight ratio of organic sunscreen agent to binder may range from about 5:1 to 1:10, preferably from about 3:1 to about 1:8, more preferably from about 2:1 to about 1:7, optimally from about 1:1 to about 1:3. Amounts of the binder may range from about 10% to about 99.5% by weight of the hydrophilic composite particles. More preferably weight of the binder may range from about 30% to about 98%, optimally from about 50 to about 85% by weight of the hydrophilic composite particles. Amounts of the sunscreen agent may range from about 0.5 to about 90%, preferably from about 2 to about 70%, optimally from about 30 to about 50% by weight of the hydrophilic composite particles.

Amounts of the hydrophilic composite particles within the cosmetic composition may range from about 0.1 to about 30%, preferably from about 2 to about 15%, optimally from about 4 to about 10% by weight of the cosmetic composition.

Average particle size of the hydrophilic particles may range from about 10 to about 2,000 nm, preferably from about 100 to about 1,500 nm, and optimally from about 200 to about 1000 nm.

Sunscreen agents according to this invention will have at least one chromophoric group absorbing within the ultraviolet ranging from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxynaphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-d ibenzoylmethane).

Particularly useful sunscreen agents are: 2-ethylhexyl p-methoxycinnamate, 4,4'-t-butyl methoxydibenzoylmethane, 2-hydroxy-4-methoxybenzophenone, octyidimethyl p-aminobenzoic acid, digalloyltrioleate, 2,2-dihydroxy-4-methoxybenzophenone, ethyl 4-[bis (hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenyl benzimidazole-5-sulfonic acid, 2-(p-dimethylaminophenyl)-5-sulfoniobenzoxazoic acid, 4-methylbenzylidene camphor, bis-ethylhexyloxyphenol methoxyphenol triazine, methylene bis-benzotriazolyl tetramethylbutylphenol, dimethicodiethylbenzal malonate, isoamyl methoxycinnamate, octyl triazone, terephthalidene dicamphor sulfonic acid and mixtures thereof.

Cosmetic compositions of this invention may not only have sunscreen agent held within but an amount of sunscreen agent may be formulated free of binder within the composition. When present outside the composite, the sunscreen agent may be available in amounts from about 0.1 to about 25%, particularly from about 2 to about 15% by weight of the composition. Some preferred embodiments of this invention may be formulated without any sunscreen agent external to the composites or with only a relatively small amount external to the composite particles. For instance, the external sunscreen agent may range in amount from about 0 to 5%, preferably from 0.01 to 2%, and possibly from 0.01 to 0.8% by weight of the composition.

A number of hydrophilic composite particles with sunscreen agent are commercially available. A first commercial material is known as "Sun Caps" sold by Particle Sciences, Inc. of Bethlehem, Pa. Average particle size is reported to be approximately 250 nm. Sun Caps 664® is sold with a concentration of octylmethoxycinnamate (OMC) of 21.5% encapsulated in a binder that includes beeswax, carnauba wax, Vinyl Pyrrolidone/Eicosene Copolymer and emulsifiers (PEG-100 stearate, PEG-20, bis-PEG-12 dimethicone, sorbitan tristearate and Steareth-100). Sun Caps® are formed in a process revealed in U.S. Pat. No. 5,733,531 herein incorporated by reference. The encapsulates are supplied as an aqueous dispersion containing up to 65% solids.

Another hydrophilic composite particulate commercially available is sold by Rona Division of EMD Chemicals under the trademark Eusolex® UV-Pearls® OMC. UV Pearls® are prepared and described in U.S. Pat. No. 7,264,795 herein incorporated by reference. These composites are sold as particulates dispersed in an aqueous carrier. The particles are octylmethoxycinnamate coated with silica, polyvinylpyrrolidone and minor ingredients. These composites are sold as a dispersion in water.

Another useful hydrophilic composite particulate according to the present invention utilizes a binder which is a condensation polymerized polyamide resin. A preferred embodiment of this binder is a polyalkyleneoxypolyamide (referred to as an PAOPA resin) and also an ester-terminated poly (ester-amide) (referred to as an EPTEA resin). The PAOPA resin can be prepared by reacting a monocarboxylic acid, a diamine compound, and a dibasic acid. The EPTEA resin can be prepared by reacting a dibasic acid, a diamine, a polyol and a mono alcohol. Preferably the EPTEA resin may be formed from reaction of: (a) at least 50 equivalent percent of the dibasic acid comprising polymerized fifty acid; (b) at least 50 equivalent percent of the diamine comprising ethylene diamine; (c) 10-60 equivalent percent of the total of the hydroxyl and amine equivalents provided by diamine, polyol and monoalcohol are provided by monoalcohol; and (d) no more than 50 equivalent percent of the total of the hydroxyl and amine equivalents provided by diamine, polyol and monoalcohol are provided by polyol. Preparation and description of these resins is found in U.S. Pat. No. 7,329,719 B2 and U.S. Pat. No. 6,492,458 herein incorporated by reference. Particularly preferred are resins under the commercial trademark Sylvaclear PA 1200V, identified by INCI name of Polyamide-3, and Sylvaclear AF 1900V sold by Arizona Chemical Company, Jacksonville, Fla. These resins are easily intimately mixed with octylmethoxycinnamate (OMC) or other organic sunscreens to form a composite particulate with photoprotective properties.

Optional Components

The composition of the present invention may contain a variety of other components to enhance physical properties and performance.

Compositions of the present invention may include a cosmetically acceptable carrier. The carrier may be a liquid or solid material. Carriers may be present in amounts ranging from about 5 to about 98%, preferably from about 20 to about 95%, optimally from about 40 to about 80% by weight of the cosmetic compositions. Water is the most common carrier for this invention. Oily carriers in the presence of water and an emulsifier will form emulsion systems as carriers. These systems may either be water-in-oil or oil-in-water emulsions. Besides water, suitable carrier classes include silicones, polyhydric alcohols, fatty alcohols, hydrocarbons, triglycerides and thickening powders.

Silicones when present may range from about 5% to about 60%, more preferably from about 5% to about 40%, by weight of the composition. These silicones may be organic, silicone-containing or fluorine-containing, volatile or non-volatile, polar or non-polar.

Particularly preferred volatile silicone oils are cyclic volatile silicones wherein the repeating unit ranges from about 3 to about 5; and linear silicones wherein the repeating unit ranges from about 1 to about 7. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids, GE 7207 and 7158 (commercially available from G.E. Silicones) and SWS-03314 (commercially available from SWS Silicones Corp.

Hydrocarbons may be useful as cosmetically acceptable carriers for compositions of this invention. They may include mineral oil, petrolatum and polyalpha-olefins. Examples of preferred volatile hydrocarbons include polydecanes such as isododecane and isodecane (e.g., Permethyl-99A which is available from Presperse Inc.) and the C7-C8 through C12-C15 isoparaffins (such as the Isopar Series available from Exxon Chemicals).

Polyhydric alcohols may serve as carriers. Illustrative of this group are propylyene glycol, dipropylene glycol, polypropylene glycol, polyethylene glycol, sorbitol, hydroxypropyl sorbitol, hexylene glycol, 1,3-butylene glycol, isoprene glycol, ethoxylated glycerol, propoxylated glycerol and mixtures thereof. Most preferred is glycerol known also as glycerin.

Fatty alcohols may also be useful carriers. The term "fatty" refers to carbon chain lengths ranging from 10 to 30 carbon atoms. Illustrative of this category are lauryl alcohol, cetyl alcohol, stearyl alcohol, isostearyl alcohol and combinations thereof.

Triglycerides are another group of materials useful as carriers. Illustrative but not limiting are sunflower seed oil, cotton oil, canola oil, soybean oil, castor oil, borage oil, olive oil, shea butter, jojoba oil and mixtures thereof. Mono- and diglycerides may also be useful. Illustrative of these categories are glyceryl monostearate and glyceryl distearate.

The optional components, when incorporated into the composition, should be suitable for use in contact with human keratinous tissue without undue toxicity, incompatibility, instability, allergic response, and the like within the scope of sound judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these classes include: abrasives, absorbents, aesthetic components such as fragrances, pigments, essential oils, skin sensates, astringents, etc. (e.g. clove oil, menthol, camphor, eucalyptus oil, eugenol, menthyl lactate, witch hazel distillate), anti-acne agents, anti-caking agents, antifoaming agents, antimicrobial agents, antioxidants, biological additives, buffering agents, bulking agents, chelating agents, chemical additives, colorants, cosmetic astringents, cosmetic biocides, denaturants, drug astringents, external analgesics, film forming polymers, opacifying agents, pH adjusters, propellants, reducing agents, sequestrants, skin bleaching and lightening agents, skin conditioning agents, skin soothing and/or healing agents and derivatives, skin treating agents, and vitamins and derivatives thereof.

In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed.

The compositions may comprise a skin lightening agent. When used, the compositions preferably comprise from about 0.1% to about 10%, more preferably from about 1% to about 7%, and optimally from about 3% to about 5%, by weight of the composition, of a skin lightening agent. Suitable skin lightening agents include niacinamide, kojic acid, arbutin, tranexamic acid, placental extract, ascorbic acid and derivatives thereof (e.g. magnesium ascorbyl phosphate, sodium ascorbyl phosphate, ascorbyl glucoside, and ascorbyl tetraisopalmitates). Other skin lightening materials suitable for use herein include Actiwhite® (Cognis), Emblica® (Rona), Azeloglicina (Sinerga) and extracts (e.g. mulberry extract). Most preferred is niacinamide, also known as Vitamin B3.

A safe and effective amount of an anti-oxidant/radical scavenger may be added in amounts from about 0.01% to about 10%, more preferably from about 0.1% to about 5% by weight of the composition.

Anti-oxidants/radical scavengers may be employed such as ascorbic acid (vitamin C) and its salts, ascorbyl esters of fafty acids, ascorbic acid derivatives (e.g. magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolor®), amines (e.g. N,N-diethylhydroxylamine, amino-guanidine), nordihydroguaiaretic acid, bioflavonoids, amino acids, silymarin, tea extracts, and grape skin/seed extracts. Preferred anti-oxidants/radical scavengers are selected from esters of tocopherol, more preferably tocopherol acetate.

The compositions of the present invention may optionally comprise a flavonoid compound. Flavonoids are disclosed in U.S. Pat. Nos. 5,686,082 and 5,686,367 herein incorporated by reference. Examples of flavonoids particularly suitable flavones, isoflavones, coumarins, chromones, discoumarols, chromanones, chromanols, isomers (e.g. cis/trans isomers) thereof, and mixtures thereof.

Preferred for use are flavones and isoflavones, in particular daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy), and mixtures thereof. Flavonoid compounds useful herein are commercially available from a number of sources, e.g., Indofine Chemical Company, Inc., Stearloids, Inc., and Aldrich Chemical Company, Inc. The herein described flavonoid compounds are preferably present in from about 0.01% to about 20%, more preferably from about 0.1% to about 10%, and even more preferably from about 0.5% to about 5% by weight.

Anti-inflammatory agents useful herein include allantoin and compounds of the Licorice (the plant genus/species *Glycyrrhiza glabra*) family, including glycyrrhetic acid, glycyrrhizic acid, and derivatives thereof (e.g. salts and esters).

The compositions may comprise a tanning active. When present, it is preferable that the compositions comprise from about 0.1% to about 20%, more preferably from about 2% to about 7% by weight of the composition. A preferred tanning active is dihydroxyacetone.

The compositions may comprise an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and even more preferably from about 0.05% to about 2% by weight of the composition.

Preferred examples of actives include those selected from the group consisting of salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cystein, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, ciclopirox, lidocaine hydrochloride, clotrimazole, climbazole, miconazole, ketoconazole, neocycin sulfate, and mixtures thereof.

The compositions may comprise a conditioning agent selected from the group consisting of humectants, moisturizers, or skin conditioners. A variety of these materials can be employed and each can be present at a level of from about 0.01% to about 40%, more preferably from about 0.1% to about 30%, and even more preferably from about 0.5% to about 15% by weight of the composition. These materials include, but are not limited to, guanidine; urea; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy compounds such as sorbitol, mannitol, glycerol, hexanetriol, butanetriol, propylene glycol, butylene glycol and hexylene glycol; polyethylene glycols; sugars and starch derivatives (e.g. alkoxylated glucose, fructose, sucrose, trehalose); hyaluronic acid; lactamide monoethanolamine; acetamide monoethanolamine; sucrose polyester; petrolatum; and mixtures thereof.

The compositions can comprise one or more thickening agents, preferably from about 0.05% to about 10%, more preferably from about 0.1% to about 5%, and even more preferably from about 0.25% to about 4%, by weight for the composition. Nonlimiting classes of thickening agents include those selected from the group consisting of:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the Carbomers, which are homopolymers of acrylic acid crosslinked with allyl ethers of sucrose or pentaerytritol. The Carbomers are available as the Carbopol® 900 series from Noveon Corporation (e.g. Carbopol® 954). In addition, other suitable carboxylic acid polymeric agents include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerythritol. These copolymers are known as Acrylates/$C_{10-30}$ Alkyl Acrylate Crosspolymers and are commercially available as Carbopol® 1342, Carbopol® 1382, Ultrez® 21, Pemulen® TR-1, and Pemulen® TR-2, from Noveon Corporation.

b. Taurate Polymers

The compositions of the present invention can optionally comprise crosslinked taurate polymers useful as thickeners or gelling agents including anionic, cationic and nonionic polymers. Examples include Hydroxyethyl Acrylate/Sodium Acryloyldimethyl Taurate (e.g. Simulgel® NS and INS 100), Acrylate/Sodium Acryloyidimethyl Taurate (e.g. Simulgel® EG), Sodium Acryloyidimethyl Taurate (e.g. Simulgel® 800) and Ammonium Acryloyidimethyl Taurate/Vinyl Pyrrolidone (e.g. Aristoflex® AVC).

c. Polyacrylamide Polymers

The compositions of the present invention can optionally comprise vinyl polymerized polyacrylamide polymers, especially nonionic polyacrylamide polymers including substituted branched or unbranched polymers. Preferred among these polyacrylamide polymers is the nonionic polymer given the CTFA designation polyacrylamide and isoparaffin and laureth-7, available under the tradename Sepigel® 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

d. Polysaccharides

A wide variety of polysaccharides are useful herein. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof.

e. Gums and Clays

Other thickening and gelling agents useful herein include materials that are primarily derived from natural sources. Nonlimiting examples include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, laponite, bentonite, hyaluronic acid, hydrated silica, hydroxypropyl chitosan, hydroxypropyl guar, karaya gum, kelp, locust bean gum, natto gum, potassium carrageenan, propylene glycol alginate, sclerotium gum, sodium carboxymethyl dextran, sodium carrageenan, tragacanth gum, xanthan gum, and mixtures thereof.

Particulate materials useful herein include but are not limited to bismuth oxychloride, sericite, mica, mica treated with barium sulfate or titanium dioxide, zeolite, kaolin, silica, boron nitride, lauroyl lysine, nylon, talc, styrene, polystyrene, ethylene/acrylic acid copolymer, aluminum oxide, silicone resin, barium sulfate, calcium carbonate, cellulose acetate, PTFE, starch, modified starches, silk, glass, and mixtures thereof. Preferred organic powders/fillers include polymeric particles chosen from the methylsilsesquioxane resin microspheres such as those sold by Toshiba Silicone under the name Tospearl 145A; the spherical particles of crosslinked polydimethylsiloxanes, especially such as those sold by Dow Corning Toray Silicone under the name Trefil E 506C or Trefil E 505C; spherical particles of polyamide and more specifically Nylon 12, especially such as those sold by Atochem under the name Orgasol 2002N Nat C05; polystyrene microspheres such as those sold by Dyno Particles under the name Dynospheres; ethylene acrylate copolymer sold by Kobo under the name FloBead EA209; PTFE; polypropylene; aluminum starch octenylsuccinate such as sold by National Starch under the name Dry Flo; microspheres of polyethylene such as those sold by Equistar under the name of Microthene FN510-00; silicone resin; platelet shaped powder made from L-lauroyl lysine, and mixtures thereof. Especially preferred are spherical powders with an average primary particle size from 0.1 to 75 microns, preferably from 0.2 to 30 microns.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLES 1-12

A series of comparison experiments were conducted to evaluate sunscreen efficacy and skinfeel properties in a number of vanishing cream compositions. Table I outlines formulas for these compositions.

TABLE I

| INGREDIENT | EXAMPLE (Weight %) | | | | | | | | | | | |
| --- | --- | --- | --- | --- | --- | --- | --- | --- | --- | --- | --- | --- |
| | 1 | 2 | 3 | 4 | 5 | 6 | 7 | 8 | 9 | 10 | 11 | 12 |
| Glycerin | 1.00 | 1.00 | 1.00 | 1.00 | 1.00 | 1.00 | 1.00 | 1.00 | 1.00 | 1.00 | 1.00 | 1.00 |
| Potassium Hydroxide (85% Assay) | 0.57 | 0.57 | 0.57 | 0.57 | 0.57 | 0.57 | 0.57 | 0.57 | 0.57 | 0.57 | 0.57 | 0.57 |
| Disodium EDTA | 0.04 | 0.04 | 0.04 | 0.04 | 0.04 | 0.04 | 0.04 | 0.04 | 0.04 | 0.04 | 0.04 | 0.04 |
| Methyl Paraben | 0.20 | 0.20 | 0.20 | 0.20 | 0.20 | 0.20 | 0.20 | 0.20 | 0.20 | 0.20 | 0.20 | 0.20 |
| Stearic Acid | 17.90 | 17.90 | 17.90 | 17.90 | 17.90 | 17.90 | 17.90 | 17.90 | 17.90 | 17.90 | 17.90 | 17.90 |
| Cetyl Alcohol | 0.53 | 0.53 | 0.53 | 0.53 | 0.53 | 0.53 | 0.53 | 0.53 | 0.53 | 0.53 | 0.53 | 0.53 |
| Propyl Paraben | 0.10 | 0.10 | 0.10 | 0.10 | 0.10 | 0.10 | 0.10 | 0.10 | 0.10 | 0.10 | 0.10 | 0.10 |
| Isopropyl Myristate | 0.75 | — | 0.75 | 0.75 | 0.75 | 0.75 | 0.75 | 0.75 | 0.75 | 0.75 | 0.75 | 0.75 |
| Octylmethoxycinnamate | 1.20 | 4.00 | 1.20 | 1.20 | — | — | — | — | — | — | — | — |
| Dimethicone | 0.50 | — | 0.50 | 0.50 | 0.50 | 0.50 | 0.50 | 0.50 | 0.50 | 0.50 | 0.50 | 0.50 |
| Micronized Titanium Dioxide | 0.20 | 0.20 | 0.20 | 0.20 | 0.20 | 0.20 | 0.20 | 0.20 | 0.20 | 0.20 | 0.20 | 0.20 |
| Niacinamide | 1.25 | 1.25 | 3.00 | 5.00 | 1.25 | 3.00 | 5.00 | 1.25 | 1.25 | 1.25 | 3.00 | 5.00 |
| Allantoin | 0.20 | 0.20 | 0.20 | 0.20 | 0.20 | 0.20 | 0.20 | 0.20 | 0.20 | 0.20 | 0.20 | 0.20 |
| Phenoxyethanol | 0.20 | 0.20 | 0.20 | 0.20 | 0.20 | 0.20 | 0.20 | 0.20 | 0.20 | 0.20 | 0.20 | 0.20 |
| Sodium Ascorbyl Phosphate | 0.20 | 0.20 | 0.20 | 0.20 | 0.20 | 0.20 | 0.20 | 0.20 | 0.20 | 0.20 | 0.20 | 0.20 |
| SunCaps 664 ® | — | — | — | — | — | — | — | — | 5.00 | — | — | — |
| UV Pearls ® | — | — | — | — | — | — | — | — | — | 3.30 | — | — |
| Sylvaclear PA 1200V ™ (1:1 with OMC) | — | — | — | — | — | — | — | — | — | 2.4 | 2.4 | 2.4 |
| Water | Bal | Bal | Bal | Bal | Bal | Bal | Bal | Bal | Bal | Bal | Bal | Bal |
| SPF Value | 3 | 7 | 3 | 3 | 1 | 1 | 1 | 15 | 13 | 15 | 15 | 15 |
| GAP Value at 103 seconds (mm × 10⁴) | 301 | — | 767 | 898 | 253 | 362 | 506 | 922 | 459 | 295 | 214 | 208 |

Test For Skinfeel Properties

A "squeeze flow under constant force" procedure is used herein to study how easily a lotion/cream is squeezed during application onto the skin. The larger the Gap Value (sample thickness), the more difficult it is to squeeze the sample. The Gap Value correlates with skinfeel properties as experienced by a consumer in applying the lotion/cream sample to skin. Gap Values must lie between tolerance limits of 175 to 350. Within the tolerance range, the lower the gap value the better the skinfeel.

The procedure is conducted utilizing a Paar Physica MCR 300 rheometer. Samples are compressed between concentric parallel plates (diameter of 25 mm for upper plate) and initial gap (vertical distance between the two plates) of 1 mm. The measurements are performed by squeezing the samples with a constant force of 12 Newton at ambient condition (23-24° C.). The time-dependence of sample thickness (gap) is measured over time and, in particular, the Gap Value recorded at 103 seconds (mmx10$^4$).

Results

Composite particles represented by SunCaps 664®, UV-Pearls® and Sylvaclear 1200V™ (1:1 with OMC) were formulated into the respective Examples 8-12 to have a total OMC sunscreen level of 1.2% by weight of the composition.

Example 1 exhibits a sun protective factor (SPF) of 3. In this composition, the sunscreen agent (OMC) is non-encapsulated. Examples 8-12 formulated with an equivalent 1.2% by weight of OMC but in encapsulated/composite format all exhibit SPF values of at least 13. Accordingly, in a stearic acid/stearate salt structuring system (i.e. a vanishing cream), there is a significant boost in photo protection utilizing an encapsulate/composite form of sunscreen.

Examples 10-12 formulated with the Sylvaclearm composite particles exhibited especially good performance. All of the Gap Values were less than 300. Accordingly, it is seen that Examples 10-12 not only exhibited a five-fold higher SPF value but also had better aesthetics (skinfeel) than those with non-composite free sunscreen agent of the Example 1-4 formulas. Further, it is noted that increasing amounts of niacinamide improved (lowered) the Gap Value without any negative effects on SPF. These effects are seen in Examples 10-12. A comparison with Examples 5-7 reveals an opposite trend wherein Gap Values increased rather than decreased as niacinamide concentration rose from 1.25% to 5%. Evidently there is a positive interaction between the Sylvaclear™composite and that of niacinamide.

What is claimed is:

1. A cosmetic composition comprising:
   (i) from 5 to 50% by weight of a $C_{12}$-$C_{20}$ fatty acid;
   (ii) from 0.1 to 20% by weight of a $C_{12}$-$C_{20}$ fatty acid salt;
   (iii) from 0.1 to 20% by weight of hydrophilic composite particles formed of an organic sunscreen agent and a binder mixed together to form the composite particles in a relative weight ratio of about 5:1 to about 1:10, the binder being a condensation polymerized polyamide resin that is a polyalkylenoxypolyamide resin;
   (iv) from 5 to 98% by weight of water;
   (v) from about 1 to about 7% by weight of niacinamide; and
   wherein the composition has a Gap Value at 103 seconds ranging from 175 to 350.

2. The composition according to claim 1 wherein the hydrophilic composite particles have an average particle size ranging from 10 to 2,000 nm.

3. The composition according to claim 1 wherein the hydrophilic composite particles have an average particle size ranging from 100 to 1,500 nm.

4. The composition according to claim 1 wherein the composition exhibits an SPF value of at least 15.

* * * * *